United States Patent [19]

Shumate, II

[11] 4,035,156

[45] July 12, 1977

[54] FILTER TYPE ROTOR FOR MULTISTATION PHOTOMETER

[75] Inventor: Starling E. Shumate, II, Knoxville, Tenn.

[73] Assignee: The United States of America as represented by the United States Energy Research and Development Administration, Washington, D.C.

[21] Appl. No.: 761,026

[22] Filed: Jan. 21, 1977

[51] Int. Cl.² .................... B04B 5/12; G01N 3/16; G01N 21/00; G01N 1/10
[52] U.S. Cl. ................... 23/259; 23/253 R; 233/26; 250/576; 356/39; 356/197; 356/246; 210/DIG. 23
[58] Field of Search ........... 23/253 R, 259; 233/26; 356/39, 197 R, 246; 250/576

[56] References Cited

U.S. PATENT DOCUMENTS

| 3,555,284 | 1/1971 | Anderson | 23/259 UX |
|---|---|---|---|
| 3,744,974 | 7/1973 | Maddox et al. | 23/259 |
| 3,798,459 | 3/1974 | Anderson et al. | 356/198 X |
| 3,864,089 | 2/1975 | Tiffany et al. | 23/259 X |
| 3,873,217 | 3/1975 | Anderson et al. | 23/259 X |
| 3,890,101 | 6/1975 | Tiffany et al. | 23/259 |
| 3,899,296 | 8/1975 | Mailen et al. | 23/259 |
| 3,901,658 | 8/1975 | Burtis et al. | 23/259 |

*Primary Examiner*—Morris O. Wolk
*Assistant Examiner*—Michael S. Marcus
*Attorney, Agent, or Firm*—Dean E. Carlson; Stephen D. Hamel; Louis M. Deckelmann

[57] ABSTRACT

A filter type rotor for a multistation photometer is provided. The rotor design combines the principle of cross-flow filtration with centrifugal sedimentation so that these occur simultaneously as a first stage of processing for suspension type fluids in an analytical type instrument. The rotor is particularly useful in whole-blood analysis.

3 Claims, 2 Drawing Figures

FILTER TYPE ROTOR FOR MULTISTATION PHOTOMETER

This invention was made in the course of, or under, a contract with the Energy Research and Development Administration.

BACKGROUND OF THE INVENTION

Several designs for rotors adapted to the analysis of whole blood have been disclosed in the past. Such rotors are used with a multistation dynamic photometer of the type having rotatable cuvets. However, each of these have some of a number of disadvantages. A recently disclosed rotor, U.S. Pat. No. 3,901,658, issued on Aug. 26, 1975, which is commonly referred to as the 3-stage, stacked rotor, required six processing and transfer functions to be performed. The step in which a high-density, immiscible liquid was added to the sedimentation bowl to displace the supernatant plasma involved difficulties related to differences in surface tension of the liquids. A small amount of carryover of the oil into the small conduits and cavities of the rotor prevented wetting of the walls by the aqueous plasma phase, with the end effect being blockage of the systems and incomplete transfer of liquids therethrough.

There exists a need for and it would be desirable to provide a simplified rotor for removing cells from whole blood whereby a multiplicity of plasma samples of equal volume can be prepared and transferred to the cuvets in a single operation prior to the addition of reagents. The present invention was conceived to meet this need in a manner to be described hereinbelow.

SUMMARY OF THE INVENTION

It is the object of the present invention to provide an improved rotor for a multistation dynamic photometer wherein cross-flow non-plugging filtration and centrifugal sedimentation occur simultaneously within the rotor as a first stage of processing for suspension type fluids in the operation of the photometer.

The above object has been accomplished in the present invention wherein in a blood analysis rotor for a multistation dynamic photometer, said rotor being of the laminated disc type having a central sample-loading port, liquid-dividing means, sample-distributing passageways, sample-receiving chambers, sample-sedimentation chambers, downstream liquid passageways, and cuvets, all in radial register, the improvement thereupon comprising filter means sealable interposed between the outlets of the sedimentation chambers and the downstream passageways, said filter means being disposed so that the entrant surfaces thereof face generally contracentripetally with respect to the axis of rotation to thus avoid collection of cells upon the filter means.

DESCRIPTION OF THE PREFERRED EMBODIMENT

Figure 2:
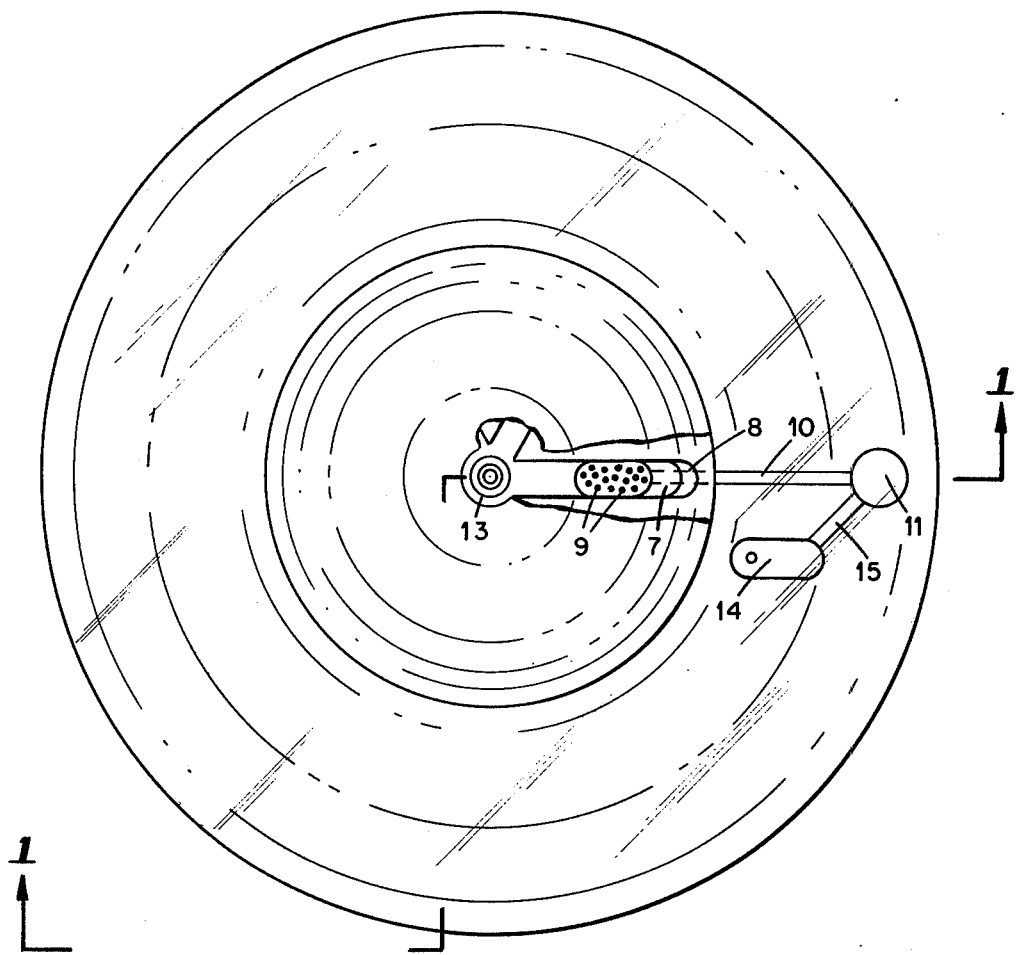
FIG. 2 is a partial top view of the rotor of FIG. 1.
Figure 1:
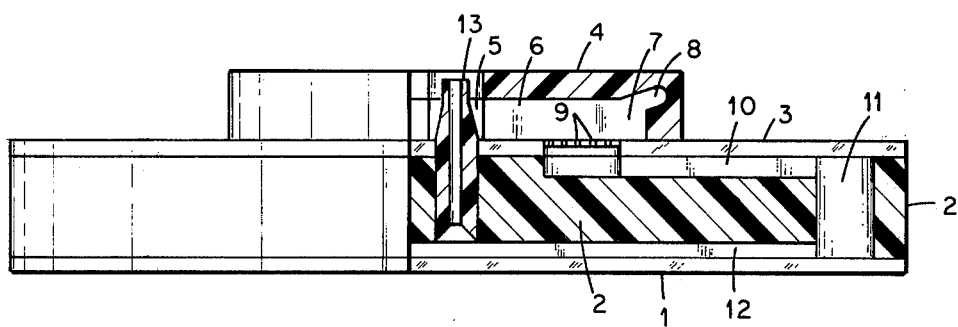
FIG. 1 is a cross-sectional cut-away view on the line 1—1 of FIG. 2 of the improved rotor of the present invention.

The rotor of a dynamic multistation photometer of the present invention as illustrated in FIGS. 1 and 2 of the drawings is a modification of the 17-place rotor as described in U.S. Pat. No. 3,798,459, issued on Oct. 6, 1972, and it should be understood that the rotor of FIGS. 1 and 2 can also be a 17-place rotor but is not necessarily limited to that many places.

The rotor of FIG. 1 comprises three UVT plastic disc laminations of equal diameter; a transparent disc-shaped base lamination 1, a matrix-plate second lamination 2, and a transparent cover plate third lamination 3. A sample-plate fourth lamination 4, of approximately one-half the diameter of the aforementioned laminations and sealably attached concentrically to the top side of the cover plate 3, provides a central sample introduction port 5, a conventional saw-tooth sample divider (not shown), and a multiplicity of equally-spaced sample passageways 6 in radial array, each leading to a respective sedimentation chamber 7, and a respective sediment sump 8. The cover plate 3 is provided with ports 9 at the sedimentation chamber 7 level, and each of the ports is provided with a micropore filter material sealably secured thereto. The filters are fixed in a plane parallel to that of the laminations. The matrix lamination 2 is machined to provide respective filtrate passageways 10 leading to respective cuvets 11, and respective return passageways 12 leading to a common central liquid return nozzle 13.

The chief difference between the prior 17-place rotor and the present rotor is in the region of the sedimentation chambers and filters. As can be seen in drawings, the sedimentation chambers 7 are located radially centrifugal to the filter membranes covering the holes 9 in order to permit the blood cells to sediment free from the filter. The upstream side of the filter membranes must face in an axial direction or in any direction not having a centirpetal component, in order that the upstream filter surfaces be maintained free from the cells. The filters were cut from Millipore RAWP 025 members filter (pore size, 1.2 $\mu$m) using a paper punch. The smallest blood cell, a platelet, is approximately 2.5 $\mu$m in diameter and therefore should be retained in this type of filter, as should erythrocytes, which are approximately 8.5 $\mu$m in diameter. The filters are then sealed over the holes 9 in the rotor using Dow Corning RTV-3145 adhesive.

In order to demonstrate the effectiveness of the above-described rotor, such a rotor was initially rotated at a speed of 400 rpm, and with the rotor spinning at this speed, 2.0 ml of a sample solution prepared by diluting a whole-blood specimen 1:10 with a saline solution (0.9 w/v % NaCl) was dynamically injected into the drop-splitting section of the rotor through the port 5 using a 2.5 ml syringe. The rotor was then accelerated to a constant speed of 2000 rpm. By using a strobe light to observe the behavior of the sample, erythrocytes were seen to amass in the sedimentation chambers while the plasma filtrate accumulated in the cuvets. The separation was complete about 15 seconds after the rotor speed had been increased to 2000 rpm. From the above test, it was clearly evident that the respective filters remained unplugged during the test such that the above-described rotor is an effective mechanism which achieves the above object of the present invention.

As illustrated in FIG. 2 of the drawings, it can be seen that the rotor is also provided with any suitable conventional means for introducing a desired reagent into the respective cuvets 11 during a complete operation of the photometer system. Such means comprise a respective reagent well 14 connected to a respective cuvet 11 by means of a respective feed tube 15. The respective wells 14 are adapted to be filled to a desired level by conventional means, not shown, as set forth in the above-mentioned patents.

The improved rotor of the present invention can be utilized in an analytical photometer system such as described in U.S. Pat. No. 3,555,284, issued Jan. 12, 1971, or in a similar miniature system such as described in U.S. Pat. No. 3,798,459, issued Mar. 19, 1974. It should be understood that when the present rotor is utilized in either of the above patented systems, the samples are introduced into the respective cuvets first after which the reagents are fed into the cuvets, and then the analysis of the resulting mixtures are carried out in a conventional manner as described in the above prior patents. The present rotor is also compatible with systems involving preloading of reagents into the cuvets.

This invention has been described by way of illustration rather than by limitation and it should be apparent that it is equally applicable in fields other than those described.

What is claimed is:

1. In a multistation dynamic photometer system provided with a rotor containing a plurality of cuvets at the outer extremity thereof, means for feeding blood plasma filtrate samples to said cuvets, means for loading reagents into said cuvets, and means for photometrically analyzing the resulting mixtures in said cuvets while said rotor is rotated at a selected high speed, said rotor being of the laminated disc-type having a central sample-loading port, liquid-dividing means, sample-distributing passageways, sample-receiving chambers, sample-sedimentation chamber provided with outlets ports, downstream liquid passageways, and cuvets, all in radial register, the improvement thereupon comprising filter means sealably interposed between the outlets of said sedimentation chambers and said downstream passage-ways, said sedimentation chambers being located radially centrifugal to said filter means and said filter means being disposed so that the entrant surfaces thereof face generally contracentripetally with respect to the axis of the rotation of said rotor to thus permit cells to sediment free from said filter means and avoid collection of said cells upon the filter means, said sedimentation chambers being provided with respective sediment sumps for collection of said cells.

2. The system set forth in claim 1, wherein said filter means is a membrane filter material having a pore size of $1.2 \mu m$.

3. The system set forth in claim 1, wherein said rotor is a 17-place rotor.

* * * * *